(12) United States Patent
Tauzin

(10) Patent No.: US 10,500,225 B2
(45) Date of Patent: Dec. 10, 2019

(54) INJECTABLE COMPOSITION; METHOD FOR PREPARING SAID COMPOSITION; USE OF SAID COMPOSITION

(71) Applicant: KH MEDTECH SARL, Geneva (CH)

(72) Inventor: Benedicte Vincente Tauzin, Bogeve (FR)

(73) Assignee: KH MEDTECH SÁRL, Geneva (CH)

( * ) Notice: Subject to any disclaimer, the term of this patent is extended or adjusted under 35 U.S.C. 154(b) by 0 days.

(21) Appl. No.: 15/781,485

(22) PCT Filed: Sep. 26, 2016

(86) PCT No.: PCT/FR2016/000151
§ 371 (c)(1),
(2) Date: Jun. 5, 2018

(87) PCT Pub. No.: WO2017/098091
PCT Pub. Date: Jun. 15, 2017

(65) Prior Publication Data
US 2018/0318335 A1   Nov. 8, 2018

(30) Foreign Application Priority Data
Dec. 7, 2015 (FR) .................................. 15 02545

(51) Int. Cl.
| | | |
|---|---|---|
| *A61K 31/728* | (2006.01) | |
| *A61K 31/20* | (2006.01) | |
| *A61K 31/19* | (2006.01) | |
| *A61K 9/00* | (2006.01) | |
| *A61K 9/127* | (2006.01) | |
| *A61L 2/00* | (2006.01) | |
| *B65B 3/00* | (2006.01) | |
| *B65B 55/02* | (2006.01) | |

(52) U.S. Cl.
CPC .......... *A61K 31/728* (2013.01); *A61K 9/0019* (2013.01); *A61K 9/127* (2013.01); *A61K 31/19* (2013.01); *A61K 31/20* (2013.01); *A61L 2/0023* (2013.01); *B65B 3/003* (2013.01); *B65B 55/02* (2013.01); *A61L 2202/21* (2013.01); *A61L 2202/23* (2013.01)

(58) Field of Classification Search
CPC ...... A61K 31/728; A61K 31/20; A61K 9/127; A61K 9/0019; B65B 3/003; B65B 55/02; A61L 2/0023; A61L 2202/23; A61L 2202/21
USPC ............................................... 514/54
See application file for complete search history.

(56) References Cited

U.S. PATENT DOCUMENTS

| | | |
|---|---|---|
| 7,741,476 B2 | 6/2010 | Lebreton |
| 8,052,990 B2 | 11/2011 | Hermitte |
| 2009/0143331 A1* | 6/2009 | Stroumpoulis ........ A61K 8/042 514/56 |
| 2009/0169615 A1* | 7/2009 | Pinsky ..................... A61K 8/14 424/450 |
| 2010/0303873 A1 | 12/2010 | Piron et al. |
| 2016/0106707 A1 | 4/2016 | Marchal et al. |
| 2018/0177819 A1 | 6/2018 | Tauzin |

FOREIGN PATENT DOCUMENTS

| | | |
|---|---|---|
| EP | 0 480 189 | 4/1992 |
| EP | 0 499 164 | 8/1992 |
| WO | WO 94/25078 | 11/1994 |
| WO | WO 97/04012 | 2/1997 |
| WO | WO 02/39977 | 5/2002 |
| WO | WO 2004/092222 | 10/2004 |
| WO | WO 2005/085329 | 9/2005 |
| WO | WO 2009/071697 | 6/2009 |
| WO | WO 2010/015900 | 2/2010 |
| WO | WO 2014/173941 | 10/2014 |
| WO | WO 2014/198406 | 12/2014 |

OTHER PUBLICATIONS

Berton et al. Involvement of Fibronectin Type II Repeats in the Efficient Inhibition of Gelatinases A and B by Long-chain Unsaturated Fatty Acids. The Journal of Biological Chemistry vol. 276, No. 23, Issue of Jun. 8, pp. 20458-20465, 2001 (Year: 2001).*
Written Opinion in International Application No. PCT/FR2016/000096, dated Aug. 23, 2016, pp. 1-7.
Farkas, J. P. et al. "The Science and Theory behind Facial Aging" *PRS GO*, Apr. 5, 2013, pp. 1-8.
Sundaram, H. et al. "Global Aesthetics Consensus: Hyaluronic Acid Fillers and Botulinum Toxin Type A—Recommendations for Combined Treatment and Optimizing Outcomes in Diverse Patient Populations" *Plastic and Reconstructive Surgery*, May 2016, pp. 1410-1423, vol. 137, No. 5.
Written Opinion in International Application No. PCT/FR2016/000151, dated Dec. 14, 2016, pp. 1-4.

* cited by examiner

*Primary Examiner* — Yih-Horng Shiao
(74) *Attorney, Agent, or Firm* — Saliwanchik, Lloyd & Eisenschenk

(57) ABSTRACT

The present invention concerns a novel, sterile and injectable aqueous composition, that is heat-sterilised, comprising at least crosslinked hyaluronic acid, or one of the salts of same, and one or more fatty acids, characterised in that the mass proportion of water is greater than 51% of the total mass, the mass proportion of fatty acid is less than 45% of the total mass, the viscoelasticity properties are such that the ratio G"/G' at 0.7 Hz is less than 0.70; a method for preparing said composition; and the use of said composition for aesthetic and therapeutic applications.

16 Claims, No Drawings

INJECTABLE COMPOSITION; METHOD FOR PREPARING SAID COMPOSITION; USE OF SAID COMPOSITION

CROSS-REFERENCE TO RELATED APPLICATION

This application is the U.S. national stage application of International Patent Application No. PCT/FR2016/000151, filed Sep. 26, 2016.

The present invention relates to:
A novel sterile injectable aqueous composition, sterilized by heat, comprising at least crosslinked hyaluronic acid, or a salt thereof, and one or more fatty acids, characterized in that:
  the mass proportion of water is greater than 51% of the total mass
  the mass proportion of fatty acid is less than 45% of the total mass
  the viscoelastic properties are such that the ratio $G''/G'$ at 0.7 Hz is less than 0.70
A method for preparing said composition
The use of said composition for aesthetic and therapeutic applications.

Hyaluronic acid is a polysaccharide formed of repeating disaccharide units of D-glucuronic acid and N-acetylglucosamine. It is linear in structure and not species specific. Hyaluronic acid is widely distributed in living humans and animals, where it fulfils many biological functions such as controlling hydration level and maintaining fluid or tissue viscoelasticity. In particular, it is found in high concentration in the synovial fluid, the vitreous body of the eye and in the skin. A 70-kg human possesses roughly 15 g of hyaluronic acid, half of which is contained in the skin, and this amount decreases with age.

Hyaluronic acid hydrogels have been known and used for many years in broad fields of aesthetics and medicine. In particular, these gels are commonly injected:
  into the eye, during ophthalmologic surgery, in order to maintain the intraocular space and to protect eye tissues
  into the joint, in the case of arthrosis, to supplement deficient synovial fluid and to temporarily restore the chondroprotective properties of said biological fluid
  into or under the skin, to fill wrinkles or to increase the volume of certain regions of the face or body.

Hyaluronic acid has a short half-life in living organisms (less than 1 week).

In many applications in aesthetics and medicine, it is injected into patients in its native form, i.e., it is not cross-linked and/or chemically modified.

For other applications, it is administered to patients in a form stabilized by cross-linking. Cross-linking considerably increases the lifespan (also called persistence) of hyaluronic acid in vivo, but it also modifies its biomechanical/rheological properties particularly by making it more elastic, which then increases its ability to create volume once injected into the target tissues.

Recent studies (e.g., Farkas et al., *Plast Reconst Surg Glob Open*, 2013, May 7, 1-8) have shown that ageing involves significant losses of volume, mainly linked to deflation of fat compartments, in the face but also in the body.

These losses of volume are also observed in diseases such as HIV, where antiretroviral treatments induce lipodystrophies that can be extremely severe.

Whether for the treatment of ageing or for the treatment of diseases, the current solutions most commonly used to restore and/or increase volumes of the face or body are as follows:
  Injection of autologous fat into the target anatomical regions. This technique has the advantage of providing long-term results (potentially near-permanent), but it requires surgery (an invasive procedure requiring fat to be taken from one region of the body and re-implanted into another region), and a significant fraction of this fat does not withstand the transfer (in general, a loss of volume of about 20 to 40% is observed in the months following surgery)
  Injection of fillers, in particular based on cross-linked hyaluronic acid. This technique, which is non-invasive and quickly performed, can be used to fill volumes over periods ranging from 3 months to more than 18 months, depending on the regions treated and the products selected.

Cross-linked hyaluronic acid thus plays a key role in the fields of aesthetics and medicine, and consequently the person skilled in the art is always seeking to improve the performance of this molecule by giving it better biomechanical and/or persistence characteristics, while retaining a very high degree of safety.

The present invention precisely aims at proposing a novel sterile injectable aqueous composition, sterilized by heat, containing at least cross-linked hyaluronic acid, or a salt thereof, and one or more fatty acids; said composition in gel form which, in particular:
  increases the safety of the injected hydrogel by improving its ability to be integrated/implanted in tissues
  considerably increases the performance of the injected hydrogel by improving in particular its ability to create more volume over time.

Therefore, the present invention concerns, according to a first of its aspects, a novel sterile injectable aqueous composition, sterilized by heat, containing at least cross-linked hyaluronic acid, or a salt thereof, and one or more fatty acids; said composition in gel form containing more than 51 mass % water and less than 45 mass % fatty acid; said composition having viscoelastic properties such that the ratio $G''/G'$ at 0.7 Hz is less than 0.70.

According to the invention, the composition contains hyaluronic acid or a salt thereof, and in particular a physiologically acceptable salt thereof, such as sodium, calcium, zinc, potassium salts, advantageously sodium salt. The hyaluronic acid can be of animal origin or obtained by bacterial fermentation. It can have a molecular mass ranging from a few daltons to several million daltons, advantageously from roughly 0.01 to 5 million daltons, more advantageously from roughly 0.1 to 3.5 million daltons, According to an aspect of the invention, the composition can be based on a hyaluronic acid derivative, i.e., based on a molecule obtained by chemical or any other modification of the hyaluronic acid molecule.

According to the invention, the total concentration of hyaluronic acid, or a salt thereof, is between 0.001 and 70 mg/ml, between 0.01 and 50 mg/ml, between 1 and 40 mg/ml, between 5 and 35 mg/ml, between 8 and 33 trig/ml, between 9 and 30 mg/ml, between 10 and 29 mg/ml, between 11 and 28 mg/ml, between 12 and 27 mg/ml, between 13 and 26.5 mg/ml, advantageously between 14 and 26 mg/ml.

According to the invention, the hyaluronic acid contained in the composition is cross-linked, preferentially according to the cross-linking techniques described in the prior art. The cross-linking agent(s) involved in the cross-linking can be identical or different. They are generally bi- or poly-functional cross-linkers of various types and they can be selected, for example, from divinylsulphone, bi- or poly-functional epoxies, carbodiimides and formaldehyde. Preferably, agents of the family of bi- or poly-functional epoxies, and in particular 1,4-butanediol diglycidyl ether (BDDE), diepoxy-octane or 1,2-bis-(2,3-epoxypropyl)-2,3-ethylene, are selected. The use of BDDE is most particularly preferred. The cross-linking temperatures are generally between about 15° C. and 60° C. and the cross-linking times are generally several hours, advantageously from more than 1 hour to about 24 hours.

According to the invention, the composition contains a mass proportion of fatty acid less than 45% of the total mass, less than 40% of the total mass, less than 35% of the total mass, less than 30% of the total mass, less than 25% of the total mass, less than 20% of the total mass, less than 18% of the total mass, less than 17% of the total mass, less than 16% of the total mass, less than 15% of the total mass, less than 14% of the total mass, less than 13% of the total mass, less than 12% of the total mass, less than 11% of the total mass, less than 10% of the total mass, less than 9% of the total mass, less than 8% of the total mass, less than 7% of the total mass.

According to the invention, the composition contains one or more fatty acids. For example, mention may be made of the following fatty acids:

saturated fatty acids: butanoic acid, pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, nonadecanoic acid, eicosanoic acid, heneicosanoic acid, docosanoic acid, tricosanoic acid, tetracosanoic acid, pentacosanoic acid, hexacosanoic acid, heptacosanoic acid, octacosanoic acid, nonacosanoic acid, triacontanoic acid, tetracontanoic acid, pentacontanoic acid, hexacontanoic acid, heptacontanoic acid, octacontanoic acid, nonacontanoic acid, hectanoic acid, dictanoic acid. Advantageously, butanoic acid (commonly called butyric acid), hexanoic acid (commonly called caproic acid), octanoic acid (commonly called caprylic acid), decanoic acid (commonly called capric acid), dodecanoic acid (commonly called lauric acid), tetradecanoic acid (commonly called myristic acid), hexadecanoic acid (commonly called palmitic acid) and octadecanoic acid (commonly called stearic acid) are selected.

monounsaturated fatty acids: dodecenoic acid, tetradecenoic acid, hexadecenoic acid, octadecenoic acid, icosenoic acid, docosenoic acid, tetracosenoic acid. Advantageously, hexadecenoic acid (commonly called palmitoleic acid) and octadecenoic acid (commonly called oleic acid) are selected.

polyunsaturated fatty acids: octadecadienoic acid, octadecatrienoic acid, octadecatetraenoic acid, icosatetraenoic acid, icosapentaenoic acid, docosapentaenoic acid, docosahexaenoic acid, Advantageously, octadecadienoic acid (commonly called linoleic acid), octadecatrienoic acid (commonly called alpha-linoleic acid), and icosatetraenoic acid (commonly called arachidonic acid) are selected.

According to an aspect of the invention, the total concentration of fatty acid is greater than 0.0001 mg/ml, greater than 0.001 mg/ml, greater than 0.01 mg/ml, greater than 0.1 mg/ml, greater than 1 mg/ml, greater than 10 mg/ml, greater than 20 mg/ml, greater than 30 mg/ml, greater than 40 mg/ml, greater than 50 mg/ml, greater than 60 mg/ml, greater than 70 mg/ml, greater than 80 mg/ml, greater than 90 mg/ml, greater than 100 mg/ml, greater than 110 mg/ml, greater than 120 mg/ml, greater than 130 mg/ml.

According to the invention, the major ingredient of the composition is water (in mass proportion), whence the qualifier "aqueous composition" for the novel composition of the invention. The water mass in the composition of the invention is greater than 51% of the total mass, advantageously greater than 60% of the total mass, advantageously greater than 70% of the total mass, advantageously greater than 75% of the total mass, advantageously greater than 80% of the total mass, advantageously greater than 85% of the total mass. A buffer solution is advantageously used in particular to better control the pH and the osmolarity of the formulation throughout its shelf-life. For example, mention may be made of the use of a buffer based on sodium chloride and phosphate ions.

According to the invention, the composition is sterile. It is sterilized according to the techniques described in the prior art. It is advantageously sterilized by heat, preferentially by moist heat (also called steam autoclaving).

Preferably, the sterilization by moist heat is carried out at a temperature above 100° C., advantageously above 110° C., advantageously above 120° C. Generally, the sterilization time can range from a few seconds to several minutes. For example, mention may be made of the following moist-heat sterilization cycles: 121° C. for 20 minutes or 125° C. for 7 minutes or 127° C. for 4 minutes or 130° C. for 3 minutes.

It is important to note that heat-sterilization is advantageously selected because it gives the selected composition a very high degree of sterility, which in turn provides a high degree of safety for the treated patient.

According to the invention, the composition is injectable. It is preferentially packaged in a syringe or a vial, so as to be easily administered through a needle or a cannula.

According to the invention, the composition has viscoelastic rheological properties such that the ratio G"/G' (=Tan δ) at a frequency of 0.7 Hz is less than 0.70, preferentially less than 0.65, more preferentially less than 0.60, more preferentially less than 0.55, more preferentially less than 0.50, more preferentially less than 0.45, more preferentially less than 0.40, more preferentially the less than 0.35.

The moduli G' (=elastic modulus) and G" (=viscous modulus), well-known to persons skilled in the art for characterizing cross-linked hyaluronic acid-based hydrogels (e.g., Sundaram et al., *Plast Reconst Surg,* 2013, 132:5S-21S), are measured using a rheometer, for example a controlled-stress rheometer, at a temperature of 25° C., with a geometry of 4 cm, by performing a frequency scan with deformation within the linear viscoelastic range.

According to the invention, the fatty acid molecules are dispersed in the hydrogel in a homogeneous or relatively homogeneous manner (dispersion of fine fatty acid droplets in the hydrogel), without forming a biphasic composition, i.e., a composition in which the aqueous phase and the organic phase are completely separate from each other (e.g., when large regions of coalescence of the organic phase within the hydrogel are observed or when the organic phase is completely above the aqueous phase of the hydrogel).

According to a preferred aspect of the invention, the composition of the invention does not contain surfactants for stabilizing the fatty acid mixture in water; these additional molecules being likely to reduce the high degree of safety imperatively required for this type of injectable formulation.

According to an aspect of the invention, the composition also comprises liposomes or niosomes containing one or more fatty acids and/or any other substance of interest for the formulation envisaged. "Substance of interest" is intended to refer to any molecule capable of providing a benefit to the composition and/or to the organism in which the composition is administered.

Liposomes and niosomes are small spherical vesicles whose wall consists of one or more lipid layers, containing an aqueous inner space. They are of interest mainly because they make it possible to vectorize substances, either by inclusion in the lipid membrane or by encapsulation in the inner membrane. For example, it is possible to encapsulate therein active principles of very different solubility (hydrophilic, amphiphilic or lipophilic).

Liposomes are obtained from natural amphiphilic molecules (phospholipids or steroids), and niosomes are composed of synthetic non-ionic amphiphilic molecules (lipopolyglycerols). Their structures are microscopic (0.01 micron to several microns).

According to an aspect of the invention, the composition of the invention contains one or more active substances of natural or synthetic origin, optionally having pharmacological action, for instance antioxidants, anti-inflammatories, antiseptics, antibacterials, antifungals, anti-cancer agents, local anaesthetics, proteins, hormones, alone or in combination. These active substances are dispersed in the hydrogel, or are grafted onto one or more of polymers of the hydrogel, or are contained/encapsulated in liposomes/niosomes dispersed in the hydrogel, or are contained/encapsulated in another material which is itself dispersed within the hydrogel.

According to an aspect of the invention, the family of fatty acids is broadened to biologically acceptable lipids, i.e., to lipids having a high degree of biocompatibility in the organism.

Therefore, according to an aspect of the invention, the novel sterile injectable aqueous composition, sterilized by heat, comprises at least cross-linked hyaluronic acid, or a salt thereof, and one or more biologically acceptable lipids, characterized in that:
  the mass proportion of water is greater than 51% of the total mass
  the mass proportion of lipid is less than 45% of the total mass
  the viscoelastic properties are such that the ratio G"/G' at 0.7 Hz is less than 0.70.

According to an advantageous aspect of the invention, the composition of the invention contains lidocaine dispersed within the hydrogel.

According to an aspect of the invention, the composition of the invention contains one or more compounds of biological origin such as cells, enriched platelets, genes, DNA fragments or growth factors. These compounds are preferentially dispersed in the hydrogel, but they can also be grafted onto one or more of polymers of the hydrogel or contained/encapsulated in liposomes/niosomes dispersed in the hydrogel or contained/encapsulated in another material which is itself dispersed within the hydrogel.

According to an aspect of the invention, the composition of the invention contains polymers which are dispersed within the cross-linked matrix of the hydrogel. For example, mention may be made of polymers of the family of polysaccharides, polyesters, polyanhydrides, polyphosphazenes, poly-ε-caprolactones, polylactic acids and derivatives thereof, polyvinyl acids, polyacrylamides, N-vinyl pyrrolidone and acrylic polymers and biologically acceptable derivatives.

According to an aspect of the invention, the composition of the invention contains mineral substances which are dispersed within the cross-linked matrix of the hydrogel. For example, mention may be made of hydroxyapatite or calcium phosphates like β tricalcium phosphate.

According to an aspect of the invention, the composition of the invention is mixed, just before administration to the patient, with one or more other, preferentially sterile substances which may provide a benefit to the organism. Mixing is thus performed by the end user, i.e., by a practitioner or by authorized personnel, by means of a suitable method using one or more mixing devices allowing a satisfactory mixture to be prepared and sterility to be maintained. For example, the end-user may mix the hydrogel of the invention and one or more compounds, such as fatty acids, lipids, active substances, biologics or mineral substances, by:
  going back and forth between two containers (one filled with the hydrogel of the invention and the other filled with the compound to be dispersed in the hydrogel), wherein said containers may be syringes, for example
  simultaneously extruding the contents of two containers (one filled with the hydrogel of the invention and the other filled with the compound to be dispersed in the hydrogel) in order to combine the various compounds and/or to mix them in another container before administration to the patient.

The objective of the novel composition disclosed in the present invention is to improve the safety and the clinical performance/efficacy of injectable cross-linked hyaluronic acid-based products by providing the following benefits in particular:
  better integration of the composition of the invention at its implantation site in the treated region. Indeed, compared to a cross-linked hyaluronic acid-based formulation of the prior art, the aqueous composition of the invention contains fatty acids (organic phase dispersed in the hydrogel), which makes it physiologically closer to the surrounding tissues, in particular when the product is injected into regions with high fat density (e.g., subcutaneous injections in the face and particularly injections to increase the volume of the cheeks or the chin). Therefore, the composition of the invention is advantageously injected into subcutaneous tissue and/or into any tissue partially or completely containing fat.

Injections of cross-linked hyaluronic acid-based gels are known to have a high degree of safety. The solution of the invention, by virtue of its enhanced ability to integrate into the surrounding tissues, is nevertheless able to significantly improve this degree of safety by reducing post-injection side effects: less inflammation due to a more favourable recognition of the implant by the body, whence less post-injection redness and/or pain, for example
  better environment provided by the composition of the invention to cells which come near and/or in contact with fatty acids; fatty acids likely to be stored within adipocyte cells, thus inducing an increase in cell volume, and/or to be used as raw materials/nourishment by cells, which can help stimulate/strengthen them
  better durability/persistence of the treatment thanks to a synergistic effect which combines the ability of the cross-linked hyaluronic acid to create volume and the ability of the fatty acids to stimulate cells. It should be noted that this synergy may be potentially increased/optimized if the fatty acids are partially or completely encapsulated (in liposomes or niosomes, for example) in order to allow them to be released over time better ability to disperse organic molecules in the composition of the invention (compared with a hydrogel based on cross-linked hyaluronic acid without fatty acid) due to the presence of an organic fraction represented by the fatty acids; which can, for example, make it possible to introduce more molecules of lipophilic nature into the product and/or to target a better homogeneity thereof the possibility of limiting the undesirable phenomenon of post-injection creation of oedema (a well-known side effect of cross-linked hyaluronic acid-based treatments) due to a reduction of inflammation at the injected region (because of better integration of the product in tissues) and/or a lower capacity of the product to swell in vivo in tissues (the presence of an organic fraction which can limit the ability of cross-linked hyaluronic acid to trap water in vivo, thus involving lower swelling of the gel in the treated region)treated region).

It is also important to note that, according to an aspect of the invention, the fatty acids can be encapsulated in liposomes/niosomes while being distributed either in the lipid bilayer or within the aqueous phase.

In this case of the encapsulation of one or more fatty acids and/or of any other substance of interest in liposomes/niosomes, the following benefits can be put forward:

maintenance of the integrity of a substance of interest within a cross-linked hyaluronic acid gel: indeed, thanks to the integration of the substance of interest in these liposomes/niosomes, the substance of interest is not degraded/oxidized, and/or does not react with the cross-linked hyaluronic acid matrix, whether during the production process of the composition of the invention or during contact with the target cells after the composition has been injected and the liposomes/niosomes have been released from the hydrogel extended release over time: the liposome/niosome (encapsulating the substance of interest), of nanometric/micrometric size, will be slowly released from the hydrogel due to the steric hindrance within the cross-linked hyaluronic acid three-dimensional network: Therefore, generally, the encapsulated substance of interest is released over longer periods relative to a simple dispersion of this substance in the cross-linked hyaluronic acid matrix: the desired biological effect (e.g., stimulation of fibroblast- and/or adipocyte-type cells) are thus more marked over time targeting of the substance of interest: once released from the cross-linked hyaluronic acid matrix, the liposome/niosome will be removed (by phagocytosis), and this endocytosis will increase the concentration of the substance of interest (e.g., fatty acid) at the cellular level (lysosomes), thus making the action of the substance of interest more effective on the target cells solubilization of poorly water-soluble substances of interest (e.g., fatty acids); the liposome/niosome thus making it possible to retain a product with only one aqueous phase. Indeed, the liposomes/niosomes, due to their vesicle-surface hydrophilicity, are able to promote the integration and the homogenization of the substance of interest in the cross-linked hyaluronic acid three dimensional matrixthree-dimensional matrix.

Surprisingly, it is important to note that the composition of the invention, by virtue of its specific features and notably its particular rheological/mechanical properties:

has a homogeneous macroscopic appearance, although consisting of water (major ingredient) and fatty acid, and this, even in the absence of emulsifier.

The fatty acids (organic phase) are dispersed in the hydrogel (aqueous phase), thus forming a gel having a homogeneous macroscopic appearance, while being microscopically heterogeneous.

Without wanting to be bound to an explanation, it may be assumed that the cross-linked hyaluronic acid, under the conditions of the invention (in particular $G''/G'<0.70$), plays the part of stabilizer of an oil-in-water emulsion forms a stable emulsion even in the case of heat-sterilization, and this even for sterilization cycles lasting several tens of minutes above 120° C.

forms an emulsion which is time-stable over a period of several months at room temperature has an extremely slow release kinetics of fatty acids out of the hydrogel; a release which may be described as delayed. Indeed, even though it is well-known to persons skilled in the art that small molecules of interest, even larger molecules above 5000 g/mol, dispersed in a cross-linked hyaluronic acid-based gel, have release kinetics of several hours (the case of lidocaine or of polyols like mannitol or glycerol), thus substantially limiting their medium- or long-term clinical efficacy; the fatty acids dispersed in the gel of the invention are released over particularly long periods of time. This feature (delayed release) imparts a considerable advantage on the hydrogel of the invention and it is obtained without reliance on restrictive and costly grafting and/or microencapsulation techniques. Without wanting to be bound to an explanation, it can be assumed that heat-sterilization plays a beneficial role for the composition of the invention by creating a particular affinity between the cross-linked hyaluronic acid and the fatty acids; affinity promoting a long-term delayed release of the fatty acids out of the hydrogel.

These surprising facts are illustrated in the examples.

Surprisingly, it is also important to note that the composition of the invention has rheological/mechanical properties (viscoelastic moduli G' and G") and cohesiveness properties similar to those of a cross-linked hyaluronic acid-based composition not containing fatty acid. These properties are described as being key in the literature for the safety and the clinical performance of an injectable cross-linked hyaluronic acid-based product (e.g., Sundaram et al., *Plast Reconst Surg*, 2013, 132:5S-21S). In other words, the addition of fatty acid, under the conditions of the invention, even in a relatively large amount, has little impact on the rheological/mechanical and cohesiveness properties of the hydrogel. This point is of particular interest because it makes it possible to offer practitioners injectable products with fatty acids which have properties similar to those already known at present and thus which can be used to treat the same indications, while aiming at better safety and clinical performance (e.g., by providing improved long-term clinical efficacy, such as the creation of tissue volume)

This surprising fact is also illustrated in the examples.

It is also important to note that the composition of the invention has a resistance to enzymatic and radical degradation (key factors of the in vivo degradation of a hyaluronic acid-based hydrogel) similar to that of the composition of the prior art not containing fatty acid. As before, this feature is advantageous because it makes it possible to offer practitioners products which can be administered for the same indications as those treated today, while providing additional benefits afforded by the combination of the cross-linked hyaluronic acid and the fatty acid under the conditions of the invention.

This surprising fact is also illustrated in the examples.

Surprisingly, it is also important to mention that the composition of the invention has an ejection force (=force needed to expel the gel from its syringe packaging through an attached needle or cannula) similar to that of a cross-linked hyaluronic acid-based composition not containing fatty acid. In other words, the addition of fatty acid, under the conditions of the invention, even in a relatively large amount, has little impact on the extrusion properties of the hydrogel. This observation is particularly surprising because the person skilled in the art would expect to obtain lower ejection forces for the composition of the invention relative to cross-linked hyaluronic acid-based compositions not containing fatty acid, knowing the lubricity of fatty acids. This point is also of interest because it makes it possible to retain suitable ejection forces familiar to the injecting practitioner, thus avoiding the injection of excessive amounts (if the ejection force were lower due to less pushing/extrusion resistance), thus limiting the undesirable effects relating to overdosage of the administered product.

This surprising fact is also illustrated in the examples.

In addition, it is important to highlight the following synergistic effects relating to the safety and to the clinical performance of the composition of the invention:

under the conditions of the invention, the cross-linked hyaluronic acid allows the fatty acids to be retained at the treated region for an efficacy over the longest term (whereas there is immediate diffusion of the fatty acids if the injection is made in solution, without hyaluronic acid), whereas the fatty acids, in turn, improve the biointegration potential of the cross-linked hyaluronic acid, which is elastic/rigid and of hydrophilic nature, in an environment consisting partially or completely of fat under the conditions of the invention, the cross-linked hyaluronic acid, by virtue of its elasticity/rigidity (small G"/G' ratio, synonymous with a highly elastic nature of the composition), is able to create mechanical stress by compression on the cells of the treated region, and particularly on fibroblast and/or adipocyte cells. As described in the literature, mechanical stress stimulates cells, thus enabling them in particular to boost and/or produce more compounds beneficial to the body, such as, for example, by producing more key components of the extracellular matrix (collagen, elastin, hyaluronic acid, etc.), which in turn enhances and/or extends the long-term effect of the injected product. Moreover, the presence of fatty acids, pushed to the cell surface, further enhances the above-described phenomenon by promoting cell stimulation, notably by serving as raw materials/nourishment and/or as catalyst for the production of beneficial compounds by the cells or by being quite simply stored within adipocyte cells (which then generates an increase in cell volume in the direction of the desired clinical effect, i.e., an increase in the volume of the treated tissues).

The present invention concerns, according to a second of its aspects, a method for preparing the novel sterile injectable composition described above.

The method for preparing the composition of the invention is characterized by the following successive steps:
a) preparation of a hydrogel based on cross-linked hyaluronic acid, or a salt thereof
b) addition of the fatty acid(s) to the hydrogel with a mixing operation
c) sterilization.

Step (a) generally begins by dissolving the hyaluronic acid and then cross-linking it, using a cross-linker, and it generally ends by purifying the hydrogel obtained.

The step of cross-linking of the hyaluronic acid is understood to refer to the step in which the hyaluronic acid chains are bridged to each other by covalent bonds. Generally, the step of cross-linking of the hyaluronic acid begins when the cross-linker is brought into contact with the hyaluronic acid and ends when the person skilled in the art considers that the reaction kinetics of the bridging of the hyaluronic acid chains by the cross-linker has reached a negligible level.

Purification of the hydrogel, in turn, allows the removal of undesirable molecules from the prepared gel, in particular cross-linking residues, following cross-linking. This purification is performed by the techniques well-known to persons skilled in the art, such as, for example, by dialysis baths, by washing with continuous water flow, or by precipitation.

The preparation of a cross-linked hyaluronic acid-based hydrogel is carried out advantageously according to the methods described in the prior art. For example, mention may be made of applications WO 97/04012, WO 2004/092222, WO 2005/085329 and WO 2009/071697 for producing a cross-linked hyaluronic acid-based hydrogel.

Step (b) consists in adding one or more fatty acids to the cross-linked hyaluronic acid-based hydrogel prepared beforehand.

With the aim of promoting homogenization of the fatty acids in the cross-linked hyaluronic acid-based hydrogel, it should be noted that these fatty acids can be heated before being added to the gel, particularly when these fatty acids are in solid form at room temperature, thus allowing their transformation into a liquid which can be dispersed in the hydrogel.

For example, this addition can be performed:
either by adding the fatty acids (in the pure state) directly to the hydrogel
or by encapsulating the fatty acid(s), for example in liposomes/niosomes
or by first preparing a solution containing the fatty acid(s) (encapsulated or not)
or by adding an additional compound onto which the fatty acid(s) has/have been grafted.

In the case of fatty acid encapsulation in liposomes/niosomes, the latter are prepared before being added to the cross-linked hyaluronic acid gel.

Several methods for preparing liposomes/niosomes of the invention may be envisaged:
traditional methods employing a step of mechanical dispersion of phospholipids, such as sonication, extrusion or microfluidization
methods based on hydration of a lipid film (the lipids and the molecules of interest to be encapsulated are first dissolved in an organic solvent and then the solvent is evaporated.

The film obtained is then hydrated in an aqueous solution)
methods based on removal of the organic solvent from an emulsion (reverse-phase evaporation)
methods relying on removal of a detergent from a solution of mixed micelles
methods based on transformation of preformed liposomes, such as lyophilization/rehydration or or freezing/thawing.

This addition of the fatty acid(s) is accompanied by a mixing operation whose purpose is to homogenize the fatty acid(s) within the hydrogel. The mixing can be done during and/or after the addition step.

The mixing operation is performed by the techniques well-known to persons skilled in the art, such as, for example, by mechanical mixing in a mixing vessel.

The mixing can be performed at a temperature above room temperature and/or under pressure and/or under ultrasound in order to optimize the homogenization of the composition.

Step (c) consists in sterilizing the composition by the techniques well-known to persons skilled in the art; the sterilization being advantageously performed with heat by autoclaving.

An advantageous method of the invention for producing a sterile injectable aqueous composition of the invention comprises at least the following steps:
preparation of an aqueous solution of hyaluronic acid
cross-linking of the hyaluronic acid
purification of the hydrogel, for example by dialysis in physiological saline
addition of one or more fatty acids with a mixing operation
packaging in syringes
sterilization.

Another advantageous method of the invention for producing a sterile injectable aqueous composition of the invention comprises at least the following steps:
preparation of an aqueous solution of hyaluronic acid
cross-linking of the hyaluronic acid
purification of the hydrogel, for example by dialysis in physiological saline
incorporation of one or more fatty acids in liposomes/niosomes and addition of these liposomes/niosomes to the hydrogel with a mixing operation
packaging in syringes
sterilization.

According to a third of its aspects, the present invention concerns the use in humans or in animals of the novel sterile injectable aqueous composition described above, for aesthetic or therapeutic applications.

The sterile injectable aqueous composition of the invention is notably used for:
filling volumes
generating spaces within certain tissues, thus promoting their optimal functioning
replacing deficient physiological liquids or tissues
stimulating or promoting tissue regeneration
hydrating and protecting tissues
delivering substances capable of providing a benefit to the organism and notably active substances and/or biologics.

By way of example, mention may be made of the uses of the hydrogel in the following cases:
formulation of a composition injectable via the intradermal or subcutaneous route for enhancing skin quality or for filling wrinkles or for restoring volumes of the face (cheekbones, chin, lips, nose, etc.) or of the body
formulation of an injectable composition for dental use, for example for filling periodontal pockets and/or for stimulating tissue regeneration around teeth
formulation of a composition injectable via the intraocular route, notably for applications during cataract, glaucoma, presbyopia or vitreous surgery
formulation of a composition injectable via the intraarticular route for applications in orthopaedics or in rheumatology, notably within the context of viscosupplementation of deficient synovial fluid for the treatment of arthrosis, but also of bone reconstruction or of cartilage regeneration
formulation of an injectable composition in urology for applications in the treatment of urinary or faecal incontinence
formulation of an injectable composition used in general medicine or surgery within the context of treatment of fibrosis or for improving wound healing
formulation of an injectable pharmaceutical composition allowing the controlled release of active substances and/or of biologics for various medical applications medical applications.

EXAMPLES

The invention now will be illustrated, in a non-limiting manner, by the following examples.

The sodium hyaluronate, fatty acids and all the other compounds used in the following examples are of high purity.

Gel extrusion is determined by measurement of the force necessary (in newtons) to eject the composition contained in a standard syringe through a 27G½ needle at a rate of 13.5 mm/min.

The rheological properties (measurement of the elastic modulus G' and of Tan $\delta$=G"/G') of the gels are measured at 25° C. using a controlled-stress rheometer (TA AR2000) and a 4 cm-2° cone/plate geometry with a 1000-micrometre gap size.

Example 1: Preparation of a Gel G1 of the Invention and of Gel REF1 (Comparative)

1.23 g of sodium hyaluronate (NaHA) powder, having a molecular mass roughly equal to 1.5 MDa and a water content of 8.2%, is weighed out and 11.3 g of a 0.25 N NaOH aqueous solution is added. Hydration of the powder lasts 1.5 hours, with regular manual homogenization with a spatula. 0.63 g of a 1,4-butanediol diglycidyl ether (BDDE) solution diluted to 1/5 in 0.25 N soda is added to the reaction mixture, followed by mechanical homogenization for 15 minutes before immersion in a thermostated bath at 50'C for 2.5 hours. A phosphate buffer solution containing HCl is added to the reticulate obtained in order to obtain a pH=7.3 and a hyaluronic acid concentration equal to 25 mg/ml. The gel is allowed to swell for 24 hours at room temperature in this solution; at the end of that time, it is manually homogenized with a spatula for 10 minutes before being purified by dialysis for 24 hours using a cellulose-based membrane (cut-off=10,000 Da) in phosphate buffer solution. The gel is manually mixed with a spatula for 10 minutes. Gel REF1A is thus obtained. The hyaluronic acid concentration of REF1A is 19.9 mg/ml.

2.7 g of palmitoleic acid is added to 15.0 g of gel REF1A. The gel is manually mixed with a spatula for 10 minutes. Gel GEL1A is thus obtained.

Gels REF1A and GEL1A are packaged in 1-ml syringes and then sterilized in an autoclave at 121° C. for 10 minutes. Gels REF1 and GEL1 (=gel of the invention), the sterilized gels derived from REF1A and GEL1A, are thus obtained.

Example 2: Preparation of a Gel G21 of the Invention and of Gel REF21 (Comparative)

8.31 g of sodium hyaluronate (NaHA) powder, having a molecular mass roughly equal to 1.7 MDa and a water content of 4.9%, is weighed out and 73.5 g of a 0.25 N NaOH aqueous solution is added. Hydration of the powder lasts 1.5 hours, with regular manual homogenization with a spatula. 4.37 g of a 1,4-butanediol diglycidyl ether (BDDE) solution diluted to 1/5 in 0.25 N soda is added to the reaction mixture, followed by mechanical homogenization for 15 minutes before immersion in a thermostated bath at 50'C for 2.5 hours. A phosphate buffer solution containing HCl is added to the reticulate obtained in order to obtain a pH=7.3 and a hyaluronic acid concentration equal to 30 mg/ml. The gel is allowed to swell for 24 hours at room temperature in this solution; at the end of that time, it is manually homogenized with a spatula for 10 minutes before being purified by dialysis for 24 hours using a cellulose-based membrane (cut-off=10,000 Da) in phosphate buffer solution. The gel is manually mixed with a spatula for 10 minutes. Gel REF2A is thus obtained. The hyaluronic acid concentration of REF2A is 25.2 mg/ml.

2.3 g of oleic acid is added to 45.0 g of gel REF2A. The gel is manually mixed with a spatula for 10 minutes. Gel GEL2A1 is thus obtained.

2.3 g of phosphate buffer solution is added to 45.0 g of gel REF2A. The gel is manually mixed with a spatula for 10 minutes. Gel REF2A1 is thus obtained.

Gels REF2A1 and GEL2A1 are packaged in 1-ml syringes and then sterilized in an autoclave at 121° C. for 10 minutes. Gels REF21 and GEL21 (=gel of the invention), the sterilized gels derived from REF2A1 and GEL2A1, are thus obtained.

Example 3: Preparation of a Gel G22 of the Invention and of Gel REF22 (Comparative)

5.1 g of a 25 mg/ml solution of sodium hyaluronate (molecular mass=1.7 MDa, water content=4.9%) in phosphate buffer solution is added to 40.0 g of gel REF2A (prepared in Example 2) and then manually mixed for 5 minutes. 8.1 g of oleic acid is then added and the gel is manually mixed with a spatula for 10 minutes. Gel GEL2A2 is thus obtained.

5.1 g of a 25 mg/ml solution of sodium hyaluronate (molecular mass=1.7 MDa, water content=4.9%) in phosphate buffer solution is added to 40.0 g of gel REF2A (prepared in Example 2) and then manually mixed with a spatula for 5 minutes. 8.1 g of phosphate buffer solution is then added and the gel is manually mixed with a spatula for 10 minutes. Gel REF2A2 is thus obtained.

Gels REF2A2 and GEL2A2 are packaged in 1-ml syringes and then sterilized in an autoclave at 131° C. for 20 minutes. Gels REF22 and GEL22 (=gel of the invention), the sterilized gels derived from REF2A2 and GEL2A2, are thus obtained.

Example 4: Preparation of Gel G23 (Gel Not Taken Into Account in the Invention Because G"/G'>0.70 at 0.7 Hz) and of Gel REF23 (Comparative)

15.0 g of a 25 mg/ml solution of sodium hyaluronate (molecular mass=1.7 MDa, water content=4.9%) in phosphate buffer solution is added to 30.0 g of gel REF2A (prepared in Example 2) and then manually mixed with a spatula for 10 minutes. 5.4 g of oleic acid is then added and the gel is manually mixed with a spatula for 10 minutes. Gel GEL2A3 is thus obtained.

15.0 g of a 25 mg/ml solution of sodium hyaluronate (molecular mass=1.7 MDa, water content=4.9%) in phosphate buffer solution is added to 30.0 g of gel REF2A (prepared in Example 2) and then manually mixed with a spatula for 10 minutes. 5.4 g of phosphate buffer solution is then added and the gel is manually mixed with a spatula for 10 minutes. Gel REF2A3 is thus obtained.

Gels REF2A3 and GEL2A3 are packaged in 1-ml syringes and then sterilized in an autoclave at 131° C. for 40 minutes. Gels REF23 and GEL23, the sterilized gels derived from REF2A3 and GEL2A3, are thus obtained.

Example 5: Preparation of a Gel G31 of the Invention 2.77 g of sodium hyaluronate (NaHA) powder, having a molecular mass roughly equal to 1.7 MDa and a water content of 4.9%, is weighed out and 27.1 g of a 0.25 N NaOH aqueous solution is added. Hydration of the powder lasts 1.5 hours, with regular manual homogenization with a spatula, 0.95 g of a 1,4-butanediol diglycidyl ether (BDDE) solution diluted to 1/5 in 0.25 N soda is added to the reaction mixture, followed by mechanical homogenization for 15 minutes before immersion in a thermostated bath at 50° C. for 3 hours. A phosphate buffer solution containing HCl is added to the reticulate obtained in order to obtain a pH=7.3 and a hyaluronic acid concentration equal at 25 mg/ml. The gel is allowed to swell for 24 hours at room temperature in this solution; at the end of that time, it is manually homogenized with a spatula for 10 minutes before being purified by dialysis for 24 hours using a cellulose-based membrane (cut-off=10,000 Da) in phosphate buffer solution. The gel is manually mixed with a spatula for 10 minutes. Gel REF3A is thus obtained. The hyaluronic acid concentration of REF3A is 18.6 mg/ml, Liposomes containing oleic acid are then prepared. To that end, the conventional technique of hydration of a lipid film followed by sonication is used.

The phospholipids used are as follows: phosphatidyl choline (PC), phosphatidyl inositol (PI) and phosphatidyl serine (PS), in a 1.0/0.5/0.1 molar ratio, respectively.

4.3 g of oleic acid and 27.8 g of the lipid mixture described above are dissolved in a chloroform/methanol mixture (50 g, 2.7:1 molar ratio). The solvents are then removed by evaporation with a rotary evaporator in the presence of argon, at room temperature, followed by drying of the phospholipids with oleic acid for 18 hours in an oven under vacuum, thus producing a film.

This film of phospholipids with oleic acid is then hydrated by adding phosphate buffer solution and by shaking. Multilamellar liposomes are thus formed, encapsulating the oleic acid. Their number-average diameter (measured by dynamic light scattering) ranges from 450 to 1200 nm.

A sonication step (ultrasound probe immersed in the multilamellar liposome mixture) at a power of 10 kHz lasting 10 minutes in an ice-water bath is used to homogenize the solution of liposomes containing oleic acid while reducing the diameter of the liposomes to number-average values ranging from 80 to 250 nm.

13.2 g of the solution of liposomes containing oleic acid prepared beforehand is added to 40.0 of gel REF3A. The gel is manually mixed with a spatula for 10 minutes. Gel GEL3A1 is thus obtained.

Gel GEL3A1 is packaged in 1-ml syringes and then sterilized in an autoclave at 121° C. for 20 minutes. Gel GEL31 (=gel of the invention), the sterilized gel derived from GEL3A1, is thus obtained.

Example 6: Preparation of a Gel G32 of the Invention

Liposomes containing palmitic acid are first prepared. To that end, the conventional technique of hydration of a lipid film followed by extrusion is used. The lipids used are as follows: phosphatidyl choline (PC), phosphatidyl glycerol (PG) and cholesterol (C), in a 1.0/0.2/0.45 molar ratio, respectively, 10.5 g of palmitic acid (first heated to transform the fatty acid in solid form at room temperature into a liquid) and 30 g of the lipid mixture described above are dissolved in a chloroform/methanol mixture (50 g, 2.7:1 molar ratio). The solvents are then removed by evaporation with a rotary evaporator in the presence of argon, at room temperature, followed by drying of the phospholipids with palmitic acid for 15 hours in an oven under vacuum, thus producing a film.

The film of phospholipids and palmitic acid is then hydrated by adding phosphate buffer solution and by shaking. Multilamellar liposomes are thus formed, encapsulating the palmitic acid. Their number-average diameter (measured by dynamic light scattering) ranges from 370 to 1050 nm.

A step of extrusion of the multilamellar liposomes on a 0.2-micron polycarbonate membrane (Avanti® Polar Lipids Mini-Extruder) at a temperature of 37° C. is used to homogenize the solution of liposomes containing palmitic acid while reducing the diameter of the liposomes to number-average values ranging from 40 to 210 nm.

3.8 g of the solution of liposomes containing palmitic acid prepared beforehand is added to 40.0 g of gel REF3A (prepared in Example 5). The gel is manually mixed with a spatula for 10 minutes. Gel GEL3A2 is thus obtained.

Gel GEL3A2 is packaged in 1-ml syringes and then sterilized in an autoclave at 121° C. for 20 minutes. Gel GEL32 (=gel of the invention), the sterilized gel derived from GEL3A2, is thus obtained.

Example 7: Characterization of Gels G1, G21, G22 of the Invention and of Gels REF1, REF21, REF22, G23 and REF23 (Comparative)

Gels G1 (prepared in Example 1), G21 (prepared in Example 2) and G22 (prepared in Example 3) of the invention are analysed and compared with gels REF1 (prepared in Example 1), REF21 (prepared in Example 2) and REF22 (prepared in Example 3) of the prior art.

All gels are analysed in terms of ejection force, rheological properties, cohesiveness and appearance, and this after sterilization in an autoclave.

The cohesiveness of the gel to be analysed is evaluated as follows: 1 ml of the gel to be tested is placed in a 10-ml bottle containing 8 ml of purified water and then manually shaken for 15 seconds. Depending on the formulations analysed, either a very high dissociation/fragmentation of the gel in water (=level 1=low cohesiveness), or very little or no dissociation (=level 3=high cohesiveness), or an average degree of cohesiveness intermediate between 1 and 3 (=level 2=average cohesiveness) can be observed.

Observation of the microscopic appearance of the gel to be analysed is made with a binocular microscope, with 40× magnification.

| Gel analysed | Ejection force | Co-hesiveness | G' (0.7 Hz) | G''/G' (0.7 Hz) | Visual appearance | Microscopic appearance |
|---|---|---|---|---|---|---|
| G1 (of the invention) | 17 N | Level 2 | 319 Pa | 0.12 | Translucent, homogeneous | Observation of small fatty acid droplets dispersed in the gel |
| G21 (of the invention) | 21 N | Level 2 | 442 Pa | <0.10 | Translucent, homogeneous | Observation of small fatty acid droplets dispersed in the gel |
| G22 (of the invention) | Not measured | Level 3 | 104 Pa | 0.51 | Translucent, homogeneous | Observation of small fatty acid droplets dispersed in the gel |
| G23 | Not measured | Level 3 | 32 Pa | 0.96 | Translucent, homogeneous | Observation of small fatty acid droplets dispersed in the gel |
| REF1 | 17 N | Level 2 | 327 Pa | 0.11 | Transparent | No small droplets observed in the gel |
| REF21 | 20 N | Level 2 | 448 Pa | <0.10 | Transparent | No small droplets observed in the gel |
| REF22 | Not measured | Level 3 | Not measured | Not measured | Transparent | No small droplets observed in the gel |
| REF23 | Not measured | Level 3 | Not measured | Not measured | Transparent | No small droplets observed in the gel |

In a completely surprising manner, it is noted that a gel based on cross-linked hyaluronic acid with fatty acid of the invention has an ejection force, a degree of cohesiveness, and rheological properties similar to those of the corresponding gel not containing fatty acid.

This feature of the gel of the invention is particularly advantageous because it makes it possible to provide practitioners injectable products with fatty acids which have properties similar to those already known at present and thus which can be used to treat the same indications, while aiming at better safety and clinical performance due to the presence of fatty acid (e.g., better ability to create/maintain volume over the long term).

Example 8: Preparation of a Solution of Non-Cross-Linked Hyaluronic Acid with Fatty Acid (Comparative)

0.35 g of oleic acid is added to 5.0 g of a 20 mg/ml solution of sodium hyaluronate (molecular mass=1.7 MDa, water content=4.9%) in phosphate buffer solution and manually mixed with a spatula for 10 minutes. Solution SOL4A is thus obtained.

Solution SOL4A is packaged in 1-ml syringes and then sterilized in an autoclave at 121° C. for 20 minutes. SOL4, the sterilized solution derived from SOL4A, is thus obtained.

At t=0 post-sterilization, it is noted that solution SOL4, translucent in appearance, has several heterogeneous regions. After 2 months of storage at room temperature, a supernatant (=organic phase of fatty acid) is observed on the surface of the solution.

This type of solution (non-cross-linked hyaluronic acid with fatty acid), not taken into account within the context of this invention, is not compatible with a shelf-life of several months due to an inadequate stability of the oil-in-water emulsion.

Without wanting to be bound to an explanation, this example shows that the hyaluronic acid must be cross-linked in order to stabilize the fatty acid(s) suspended in the hydrogel, which then makes it possible to obtain a composition of the invention having a homogeneous visual appearance while being microscopically heterogeneous.

Example 9: Evaluation of Resistance to Radical and Enzymatic Degradation for Gel G21 of the Invention and for Gels REF21 and REF21+Antioxidant 4% mannitol is added to 4.9 g of gel REF21 and then manually mixed with a spatula for 10 minutes. Gel [REF21+antioxidant] is thus obtained.

Test of radical degradation:

The following are placed, respectively, in 5 test tubes (1 minute of manual mixing with a spatula performed for each test tube):
tube 1: 2.0 g of gel G21 (prepared in Example 2)
tube 2: 2.0 g of gel REF21 (prepared in Example 2)
tube 3: 2.0 g of gel G21+10% of $H_2O_2$ solution (30% mass/mass)
tube 4: 2.0 g of gel REF21+10% of $H_2O_2$ solution (30% mass/mass)
tube 5: 2.0 g of gel [REF21+antioxidant]+10% of $H_2O_2$ solution (30% m/m).

These tubes are then placed in an oven at a temperature of 37° C.; for 6 hours and then all the tubes are turned over.

It is noted that the contents of tubes 1 and 2 flow out very little and in the same manner, whereas the contents of tubes 3 and 4 flow out quickly and in the same manner. In turn, the contents of tube 5, with antioxidant, flow out in an intermediate manner between tubes 1/2 and tubes 3/4.

This experiment shows that, during radical degradation by $H_2O_2$, the gel of the invention and the corresponding gel without fatty acid have similar degradation kinetics.

Test of enzymatic degradation:

The following are placed, respectively, in 4 test tubes (1 minute of manual mixing with a spatula performed for each test tube):
tube 1: 2.0 g of gel G21 (prepared in Example 2)
tube 2: 2.0 g of gel REF21 (prepared in Example 2)
tube 3: 2.0 g of gel G21+10% of hyaluronidase solution (bovine origin, 200 U/ml)
tube 4: 2.0 g of gel REF21+10% of hyaluronidase solution (bovine origin, 200 U/ml).

These tubes are then placed in an oven at a temperature of 37° C. for 6 hours and then all the tubes are turned over.

It is noted that the contents of tubes 1 and 2 flow out very little and in the same manner, whereas the contents of tubes 3 and 4 flow out quickly and in the same manner.

This experiment shows that, during enzymatic degradation by hyaluronidases, the gel of the invention and the corresponding gel without fatty acid have similar degradation kinetics.

Example 10: Evaluation of the Time-Stability of Gels G1, G21, G22 of the Invention and of Gel G23 During Storage at Room Temperature (Comparative)

Gels G1 (prepared in Example 1), G21 (prepared in Example 2), G22 (prepared in Example 3) and G23 (prepared in Example 4) are stored at room temperature and observed over time.

| Gel stored at RT° C. | t = 0 | t = 3 months | t = 6 months |
|---|---|---|---|
| G1 (of the invention) | Homogeneous translucent gel | Homogeneous translucent gel | Homogeneous translucent gel |
| G21 (of the invention) | Homogeneous translucent gel | Homogeneous translucent gel | Homogeneous translucent gel |
| G22 (of the invention) | Homogeneous translucent gel | Homogeneous translucent gel | Homogeneous translucent gel |
| G23 | Homogeneous translucent gel | Homogeneous translucent gel | Translucent gel but heterogeneous regions are observed |

It is noted that, after 6 months at room temperature, gels G1, G21 and G22 of the invention are translucent and homogeneous whereas gel G23 (=gel not taken into account in the invention), having a ratio G"/G' at 0.7 Hz greater than 0.70, starts to show heterogeneous regions (coalescence of small fatty acid droplets within the gel).

Unlike gels G1, G21 and G22 of the invention, gel G23 is not compatible with a shelf-life of 24 months at room temperature, the duration generally required by practitioners (users) for injectable cross-linked hyaluronic acid-based products.

The ratio G"/G' at 0.7 Hz, synonymous with a substantially elastic nature of the viscoelastic composition, thus plays a determining role in the present invention.

Example 11: Evaluation of the Kinetics of Fatty Acid Release (Comparative)

The following are placed on cellulose-based membranes (membrane cut-off=10,000 Da; filling ratio of roughly 3.5 g of gel per cm of membrane):
10 g of gel G1 of the invention (prepared in Example 1)
10 g of gel REF1 (prepared in Example 1)
10 g of gel G22 of the invention (prepared in Example 3)
10 g of gel REF22 (prepared in Example 3).

These 4 membranes are each placed in 500 ml of 0.9% NaCl saline solution and the gels are observed over time:
at t=0, gels G1 and G22 of the invention are translucent due to the presence of fatty acids dispersed in the gel. This point is further confirmed by observation with a binocular microscope, with 40× magnification, allowing visualization of the small fatty acid droplets dispersed in the cross-linked hyaluronic acid gels. As for gels REF1 and REF22, they are completely transparent the same observations are performed (visual and binocular microscope) after 1 day, 3 days, 1 week, 2 weeks, 3 weeks, 4 weeks, 6 weeks, 8 weeks, 24 weeks and 40 weeks. For each of these time points, as at t=0, gels G1 and G22 of the invention are translucent and gels REF1 and REF22 are transparent.

In a completely surprising manner, even though it is well-known to persons skilled in the art that small- to medium-sized molecules are quickly released from a cross-linked hyaluronic acid-based gel (e.g., lidocaine hydrochloride molecule almost totally released within the first 24 hours—Example 4 of WO 2010/015900), it is noted that the fatty acids present in the gels of the invention are released very little, if at all, after several weeks. This feature imparts a considerable advantage to the hydrogels of the invention because it allows them to benefit from the advantages provided by the synergy between the cross-linked hyaluronic acid and the fatty acids, under the conditions of the invention, over very long periods of time after implantation in tissues.

The invention claimed is:

1. A sterile injectable hydrogel composition, sterilized by autoclaving, comprising at least cross-linked hyaluronic acid, or a salt thereof, and one or more fatty acids, wherein:
   a) the mass proportion of water is greater than 51% of the total mass;
   b) the mass proportion of fatty acid is less than 18% of the total mass and the total concentration of fatty acid is greater than 0.0001 mg/ml; and
   c) the viscoelastic properties are such that the ratio $G''/G'$ at 0.7 Hz is less than 0.70, wherein the fatty acid molecules are dispersed in the hydrogel of said cross-linked hyaluronic acid in a homogeneous manner.

2. The composition of claim 1, wherein the hyaluronic acid or a salt thereof is sodium hyaluronate.

3. The composition of claim 1, wherein the hyaluronic acid or a salt thereof is cross-linked using a bi- or polyfunctional cross-linker.

4. The composition of claim 1, wherein the hyaluronic acid or a salt thereof is cross-linked using 1,4-butanediol diglycidyl ether (BDDE).

5. The composition of claim 1, wherein the total concentration of hyaluronic acid or a salt thereof is between 9 and 30 mg/ml.

6. The composition of claim 1, wherein the mass proportion of water is greater than 80% of the total mass.

7. The composition of claim 1, wherein the mass proportion of water is greater than 85% of the total mass.

8. The composition of claim 1, wherein the fatty acid(s) is/are selected from the group consisting of butyric acid, caproic acid, caprylic acid, lauric acid, myristic acid, palmitic acid, stearic acid, palmitoleic acid, oleic acid, linoleic acid, alpha-linoleic acid and arachidonic acid.

9. The composition of claim 1, wherein the total concentration of fatty acid is greater than 0.1 mg/ml.

10. The composition of claim 1, wherein the composition contains liposomes or niosomes.

11. The composition of claim 1, wherein at least a portion of the fatty acids is contained in liposomes or niosomes.

12. The composition of claim 1, wherein the viscoelastic properties are such that the ratio $G''/G'$ at 0.7 Hz is less than 0.45.

13. A method for preparing a sterile injectable hydrogel composition of claim 1, comprising at least cross-linked hyaluronic acid, or a salt thereof, and one or more fatty acids, the method comprising at least the following successive steps:
   a) preparation of a hydrogel based on cross-linked hyaluronic acid, or a salt thereof;
   b) addition of the fatty acid(s) to the hydrogel with a mixing operation, such that the fatty acid molecules are dispersed in the hydrogel of said cross-linked hyaluronic acid, in a homogeneous or relatively homogeneous manner; and
   c) sterilization.

14. The method for preparing a sterile injectable hydrogel composition comprising at least cross-linked hyaluronic acid, or a salt thereof, and one or more fatty acids, of claim 13, the method comprising at least the following successive steps:
   preparation of an aqueous solution of hyaluronic acid;
   cross-linking of the hyaluronic acid;
   purification of the hydrogel;
   addition of one or more fatty acids with a mixing operation;
   packaging in syringes; and
   sterilization.

15. A method of aesthetically or therapeutically treating a patient comprising the administration of a composition of claim 1 to a patient in need of aesthetic or therapeutic treatment.

16. The composition of claim 1, wherein the fatty acid is oleic acid.

* * * * *